(12) United States Patent
Farone et al.

(10) Patent No.: US 6,756,046 B2
(45) Date of Patent: Jun. 29, 2004

(54) POLYOL ESTER INSECTICIDES

(75) Inventors: William A. Farone, Irvine, CA (US); Tracy Palmer, Rancho Santa Margarita, CA (US); Gary Joseph Puterka, Sheperdstown, WV (US)

(73) Assignee: Ava Chemical Ventures L.L.C., Portsmouth, NH (US)

( * ) Notice: Subject to any disclaimer, the term of this patent is extended or adjusted under 35 U.S.C. 154(b) by 35 days.

(21) Appl. No.: 10/132,490

(22) Filed: Apr. 24, 2002

(65) Prior Publication Data

US 2002/0192257 A1 Dec. 19, 2002

Related U.S. Application Data

(63) Continuation-in-part of application No. 09/504,016, filed on Feb. 18, 2000, now Pat. No. 6,419,941.

(51) Int. Cl.[7] .............................................. A01N 25/02
(52) U.S. Cl. ........................ 424/406; 424/405; 514/25; 514/546
(58) Field of Search ................................ 424/405, 406; 514/25, 53, 546, 549

(56) References Cited

U.S. PATENT DOCUMENTS

| | | | |
|---|---|---|---|
| 5,290,751 A | * | 3/1994 | Fiard et al. ................. 504/116 |
| 5,489,433 A | * | 2/1996 | Aboud ........................ 424/405 |
| 5,756,716 A | | 5/1998 | Farone et al. ................ 536/720 |

OTHER PUBLICATIONS

Puterka er al., *J. Econ. Entomol.* 88(3), 615–619 (1995).
Thurston et al., *Ent. exp. & appl.* 5, 233–238 (1962).
Parr et al., *J. Econ. Entomol.* 61(6), 1525–1531 (1968).
Siegler et al., *J. Econ. Entomol.* 18, 292–299 (1925).
Chortyk et al., *J. Agric. Food Chem.* 44, 1551–1557 (1996).
Neal et al., *J. Econ. Entomol.* 87(6), 1600–1607 (1994).
Thurston, *J. Econ. Entomol.* 63(1), 272–274 (1970).
Imai et al., *Appl. Entomol. Zool.* 29(3), 389–393 (1994).
Adamson, *Physical Chemistry of Surfaces* 3rd Ed., 504–507 (1976).

* cited by examiner

*Primary Examiner*—Neil S. Levy
(74) *Attorney, Agent, or Firm*—Cynthia H. O'Donohue

(57) ABSTRACT

The present invention relates to an environmentally acceptable synthesis method of polyol esters that produces no toxic by-products methods during the synthesis and the resultant esters are environmentally friendly insecticides. The present invention also provides for the use of these esters in a mixture as safe effective insecticides.

14 Claims, No Drawings

POLYOL ESTER INSECTICIDES

This application is a continuation-in-part of applicant's application U.S. Ser. No. 09/504,016, filed Feb. 18, 2000 now U.S. Pat. No. 6,419,941, and entitled "Improved Polyol Ester Insecticides and Method of Synthesis".

STATEMENT REGARDING FEDERALLY SPONSORED RESEARCH AND DEVELOPMENT

The U.S. Government has a paid-up license in this invention and the right in limited circumstances to require the patent owner to license others on reasonable terms as provided for by the terms of Grant 99-33610-7466 awarded by U. S. Department of Agriculture.

FIELD OF THE INVENTION

The present invention relates to the use of a mixture of polio esters as insecticides to eliminate or reduce plant pests. More particularly, this invention concerns a mixture of sugar esters which have insecticidal activity and which are environmentally friendly.

BACKGROUND OF THE INVENTION

The following description of the background of the invention is provided to aid in understanding the invention, but is not admitted to be, or to describe, prior art to the invention. All publications are incorporated by reference in their entirety.

Sucrose octanoate has proven to be a useful insecticide compound. Varieties of sucrose esters are contained in the natural wax of leaves. Discussions of these esters may be found, for example, in Neal, J. W. Jr. et al, J. Econ. Entomol. 87, 1600–1607(1994); Puterka, G. J., et al, J. Econ. Entomol. 88, 615–619(1995), and Lui, T. X. et al, J. Econ. Entomol. 89, 1233–1239 (1996). Sucrose octanoate is contained in the mixture of sucrose esters made when coconut fatty acids are used to make sucrose esters. The sucrose esters are readily biodegradable and hydrolyze to readily metabolizable sucrose and fatty acid. Sucrose esters can be made by the methods disclosed in U.S. Pat. 5,756,716, William A. Farone and Robert Serfass, "Method for Production of Sugar Esters", May 26, 1998. Other methods for making these compounds are also known and referenced in this patent.

The efficient production of sucrose octanoate involves several steps, including an esterification, a transesterification and then a purification step. It would be extremely useful to have compounds with similar insecticidal activity, similar environmental acceptability, made from similar natural products, that could be synthesized in fewer steps. Unfortunately there is no means of predicting the chemical structures that will have insecticidal activity. There is no general agreement as to exactly how the sugar ester compounds obtain their insecticidal activity.

One hypothesis is that the compounds like sucrose laurate or sucrose octanoate act as surfactants to dewax the insect's protective coating. The insect then either dehydrates or is readily attacked by microbes. This hypothesis is supported by the observation that the compounds are "contact" insecticides. Since the sucrose esters are constituents of plant leaves, there is another hypothesis that the compounds somehow interfere with the metabolism of the insect to prevent them from eating the tissue that the esters protect. This hypothesis requires ingestion of the material by the insect and cannot be ruled out since "contact" can also result in ingestion.

It is also known that the short chain sucrose esters that are effective as insecticides have certain properties that seem to enhance that activity. Chortyk and co-workers at the United States Department of Agriculture [see Chortyk, O. T., Pomonis, J. G., and Johnson, A. W., J. Agric. Food Chem., 44, 1551–1557 (1996)] concluded that the sucrose esters with fatty acid chain lengths below 12 were more effective especially when there were 2 or 3 side chains on the sucrose. The fact that there are eight hydroxyl groups that can be esterified in sucrose means that, in principal, one can make 8 sucrose monoester, 28 diester and 56 triester isomers. It is unpredictable if all esters of one type (e.g. monoesters, diesters, etc.) are equally effective. Molecular orbital calculations performed in the inventors' laboratory suggest that not all esters are equally likely to be produced during synthesis.

Definitions

In accordance with the present invention and as used herein, the following terms are defined with the following meanings, unless explicitly stated otherwise.

The term "enhanced" refers to increasing or improving a specific property.

SUMMARY OF THE INVENTION

In one aspect the present invention relates to a new environmentally friendly polyol ester insecticide. The inventors unexpectedly found that a mixture of polyol esters has a greater insecticidal activity than the individual components or what one could reasonably anticipate from an additive effect.

More particularly another aspect of this instant invention is the use of these esters as safe effective insecticides. The inventors found the surprising and unexpected result that a mixture of octanoic acid (C8) esters is more effective as insecticides, and that a mixture of sucrose and sorbitol acid esters were the most effective.

Also there was the surprising finding that for sucrose octanoate mixture the use of an alcohol solvent including but not limited to such alcohols as butanol, propanol, ethanol, methanol, and the likes, added at low concentrations provided a composition that was shown to be even more effective as an insecticide than sucrose octanoate alone.

DETAILED DESCRIPTION OF THE INVENTION

The method of preparation of the polyol esters, in particular sorbitol, of this invention is best explained in terms of 7 steps. One of the objects of the preparation method is have an environmentally acceptable synthesis that produces no toxic by-products. Without limiting the scope of this invention as expressed by the claims which follow, the synthesis steps will be discussed briefly.

The process is basically as follows:

1. The desired organic acid (e.g. octanoic, deconoic, but not limited to these) is charged to the reactor at a temperature sufficiently high to keep it in liquid form.
2. The polyol (e.g. either xylitol or sorbitol) is added in an amount that would allow the production of the monoester stoichiometrically plus an additional 10% to drive the reaction essentially to completion.
3. An esterification catalyst is added. Any usual catalyst can be used such as sulfuric acid or phosphoric acid. Phosphoric acid is the preferred embodiment in this case since neutralization at the completion of the reaction provides a phosphate salt that can either be left in the product (since phosphorous is an essential plant nutrient and phosphates are a known method of providing phosphorus) or removed by filtration if desired (whereupon the salt can be sold separately for fertilizer use).

4. The reactor is held at a temperature sufficiently high along with a pressure sufficiently low to allow water to be removed as the esterification reaction proceeds. For most of the esters a temperature around 150° C. and atmospheric pressure was used.

5. The reaction is allowed to proceed until the remaining organic acid reaches a low equilibrium value. This point can be determined very simply by monitoring the free acid content of the reaction mixture and comparing differing reaction times (see Example 1 and 2). When the free organic acid is reduced no further the reaction is essentially completed. The equilibrium value in weight percent depends on the molecular weight of the organic acid and the structure of the isomers formed. Once determined for a particular organic acid and polyol combination it can be used as a measure of reaction completion.

6. At the completion of the reaction (approximately 18–30 hours for the esters synthesized for the insecticidal studies) the solution is neutralized with an amount of base that is sufficient to neutralize all of the mineral acid used as a catalyst plus bring the solution to a desired pH for subsequent use. If calcium hydroxide is used as the base, calcium phosphate can be filtered out of the product. Other bases could be used depending on the desired nature of the final product. This procedure was followed to allow for a product of good water solubility with little or no residual fine solid particles.

7. The product (filtrate from Step 6) is analyzed and is ready for use.

This procedure of this present invention is deliberately made deceptively simple. Due to the fact that the insecticide nature as well as other properties of these materials change depending on the isomers it is desired to have a simple process that can be repeated with little difficulty. The only "waste product" of the reaction is the water removed during the esterification. The equipment and reaction conditions are selected in such a manner that the tendency of any of the organic acid to distill over with the water is thwarted by the use of appropriate reflux allowing the water to be removed and the acid to fall back into the reactor. Thus, in the preferred method a distillation column (tray or packed column) is used over the reactor to insure retention of the acids.

Sucrose octanoate is synthesized by the method described in U.S. Pat. 5,756,716, incorporated herein by reference. The resultant product, sucrose octanoate, is found to have monoesters that are more effective as insecticides than the diesters and triesters of sucrose octanoate. This finding is in contradiction to the finding of Chortyk. The inventors of the above described process find the method of synthesis is important in defining the distribution of isomers in complex molecules with the subsequent result that one must either specify the exact nature of the isomers involved and/or the method of synthesis as a mean of selecting the best insecticides.

In the sucrose studies the octanoate was found to be the approximately optimal chain length. Octanoic acid is a reasonably abundant fatty acid fraction of natural oils (e.g. coconut oil) after the oil is "split", i.e. hydrolyzed to glycerol and fatty acids. Nature prefers even chain fatty acids. Although the odd chain fatty acids are also likely to be reasonably effective it is the inventors' purpose to make the biodegradation products as natural as possible. It is well known that the long chain fatty acid esters of sucrose (e.g. sucrose stearate) are extremely mild materials with excellent surfactant properties. These materials have been used as food emulsifiers for many years.

A wide variety of compounds were synthesized. The compounds that were proven to have the best activity when compared to sucrose octanoate are sorbitol and xylitol esters of short chain fatty acids, particularly the octanoic and decanoic acid monoesters. These compounds are more easily prepared than the sucrose octanoate. They can be synthesized directly from the raw materials in a single step using only a neutralizable mineral acid as a catalyst in the process described earlier. Due to the greater ease of synthesis these materials could be less expensive even if they are slightly less effective than sucrose octanoate.

The following are examples of making polyol esters according to the present invention. Other polyol esters may also be made using the process of this invention.

Examples 1 and 2 were run to compare different times for the degree of conversion. This type of benchmark reaction can be performed to determine optimal conditions for other polyol esters.

EXAMPLE 1

Preparation of sorbitol octanoate: 432.44 grams of octanoic acid was put into a 2-liter round bottom, three-neck flask with a short distillation head. A mechanical stirrer was connected and 598.51 grams of sorbitol was slowly added. The catalyst in the reaction was phosphoric acid and 30.93 grams were added. A temperature controller and heating mantle were attached and the temperature of the reaction was set at 150° C. The reaction was stopped after 21 hours. The phosphoric was neutralized with 26.02 grams of calcium hydroxide. The solution was filtered to remove the calcium phosphate precipitate. The density of the product was 1.4 g/cc and the free acid was 6.40%. The degree of reaction completion was thus about 85.5%

EXAMPLE 2

Preparation of sorbitol octanoate again. 438.52 grams of octanoic acid, 600.10 grams of sorbitol and 32.122 grams of phosphoric acid was placed into a round bottom flask with a mechanical stirrer and short distillation head attached. The temperature was set at 150° C. The reaction proceeded until the free acid value was 3.88%. Total reaction time was 28 hours. The phosphoric acid was neutralized with 27.015 grams of calcium hydroxide. The product was analyzed and the density was 1.4 g/cc and the ash was 2.33%. The degree of reaction is thus 91.3%

EXAMPLE 3

Sorbitol decanoate was prepared by adding 380.80 grams of sorbitol and 302.0 grams of decanoic acid to a one-liter round bottom flask. 27.14 grams of 75% phosphoric acid were added. The agitator was turned on and the temperature was set to 150° C. The total reaction time was seven hours and ten minutes. The phosphoric acid was neutralized with 22.83 grams of calcium hydroxide and the solution as filtered to remove the calcium phosphate. The final product was analyzed and the free acid remaining was 7.50%. The density was 1.05 g/cc and the ash value was 1.00%. The degree of reaction completion was thus 76.0%.

The following are examples of sucrose octanoate and sorbitol octanoate mixtures and their effectiveness as insecticides.

EXAMPLE 4

Sucrose Octanoate and Sorbitol Octanoate Composition

Sucrose octanoate and sorbitol octanoate were mixed with a carrier such as water wherein the ratio of the two octanoates in the mixture was 50:50 and the total octanoates concentration was at least 40% of the initial formulation before dilution. The initial composition was diluted with water such that the octanoates concentration was 40, 200, 400, 1200, 2400, 3200 and 4000 ppm of octanoates in the mixture. This composition was used to treat Pear Psylla for four replicate applications.

Table 1 contains the results of the application of two control solutions, sorbitol octanoate alone and sucrose octanoate alone. These tests were performed at the same time the combination was tested.

TABLE 1

| Level ppm | 1 hr Kill Percentage | | 24 hr Kill percentage | |
|---|---|---|---|---|
| | Sorbitol octanoate | Sucrose octanoate | Sorbitol octanaote | Sucrose octanoate |
| 40 | 2.14 | 20.48 | 8.39 | 28.18 |
| 200 | 10.17 | 29.09 | 27.65 | 34.52 |
| 400 | 4.97 | 24.21 | 30.52 | 32.94 |
| 1200 | 31.01 | 29.3 | 63.82 | 55.79 |
| 2400 | 57.59 | 21.29 | 79.10 | 60.71 |
| 3200 | 60.90 | 33.67 | 90.18 | 73.28 |
| 4000 | 67.83 | 47.54 | 94.30 | 79.62 |

Table 2 details the effect of applying a solution (Solution 1) that is a ratio of 50:50 sorbitol octanoate to sucrose octanoate wherein the total active ingredients are 40% of the total composition prior to dilution. The ratio of active ingredients for solution 2 is 75% sorbitol octanoate to 25% sucrose octanoate. The ratio of active ingredients for solution 3 is 87.5% sorbitol octanoate to 12.5% sucrose octanoate. All of the solutions contained 40% total active ingredients in the concentrate prior to dilution for use.

TABLE 2

| Level ppm | 1 hr Kill Percentage | | | 24 hr Kill Percentage | | |
|---|---|---|---|---|---|---|
| | Solution 1 | Solution 2 | Solution 3 | Solution 1 | Solution 2 | Solution 3 |
| 40 | 4.55 | 33.94 | 37.80 | 16.69 | 40.39 | 38.73 |
| 200 | 25.84 | 10.56 | 4.91 | 38.41 | 26.93 | 25.11 |
| 400 | 19.42 | 33.96 | 36.20 | 44.36 | 47.18 | 61.54 |
| 1200 | 19.82 | 31.68 | 32.38 | 58.20 | 70.56 | 62.58 |
| 2400 | 48.35 | 40.17 | 72.38 | 86.19 | 69.68 | 90.45 |
| 3200 | 61.92 | 77.79 | 72.77 | 90.40 | 95.24 | 94.85 |
| 4000 | 90.52 | 84.81 | 65.12 | 95.36 | 99.34 | 92.26 |

It can be seen that the mixtures in Table 2 are unexpectedly better than the individual components. Surprisingly there was an improvement in kill percentage using the mixtures particularly at the shorter times and higher concentrations. For example, the 75:25 ratio of sorbitol octanoate to sucrose octanoate (solution 2) increased the kill percentage from 33.67% (sucrose octanoate only) or 60.9% (sorbitol octanoate only) to 77.79% at 3200 ppm for 1 hour and from 47.54% and 67.83% to 84.81% at 4000 ppm for 1 hour. Similar changes can be seen at 24 hours and for the other formulations.

EXAMPLE 5

Combinations of Sucrose Octanoate with Butanol

Butanol is a solvent used in the manufacturing process and it has not been known to provide insecticidal activities at extremely low doses such as are used here. Alcohols may kill insects when used full strength; however, low doses in the 100 ppm range are not known to have any insecticidal activity.

In this example three solutions were made using a base formulation containing 40% sucrose octanoate in the concentrate. Solution 1 was a control of only sucrose octanoate. Solution 2 contained 4.49% butanol added to the sucrose octanoate and solution 3 contained 8.89% butanol added to the sucrose octanoate. The three solutions were diluted with water such that there was either 1200 ppm or 3200 ppm of active ingredient (sucrose octanoate) in each of the solutions. Tobacco Aphids were treated with the dilute solutions and the kill of Aphids was measured after 1 hour and 24 hours in replicate trials. The average kill percentages are reported in the Table 3.

TABLE 3

| Level ppm | 1 hr Kill Percentage | | | 24 hr Kill Percentage | | |
|---|---|---|---|---|---|---|
| | Solution 1 | Solution 2 | Solution 3 | Solution 1 | Solution 2 | Solution 3 |
| 1200 | 13.63 | 16.48 | 24.39 | 30.71 | 48.52 | 72.35 |
| 3200 | 63.24 | 93.15 | 90.20 | 79.95 | 99.45 | 96.14 |

In all cases the formulations to which butanol was added had an enhanced kill effect with the effect being greater for the higher level of butanol and the higher application rate.

EXAMPLE 5

Combinations of Sorbitol Octanoate and Sorbitol Decanoate

Mixtures of sorbitol octanoate and sorbitol decanoate were tested against the 2-Spotted Mite. The tests were replicated six times and the kills after 1 hour were recorded. The control tests for the pure sorbitol decanoate and sorbitol octanoate performed at the same time are given in Table 4.

TABLE 4

| Level ppm | 1 hr kill | |
|---|---|---|
| | Sorbitol decanoate | Sorbitol octanoate |
| 40 | 37.45 | 38.04 |
| 200 | 45.29 | 33.07 |
| 400 | 56.61 | 45.72 |
| 1200 | 66.28 | 44.24 |
| 2400 | 77.50 | 69.27 |
| 3200 | 76.72 | 72.60 |
| 4000 | 81.97 | 73.18 |

Three formulations were tested at the same time as the controls and the results are detailed in Table 5. Solution 1 contained a ratio of 50:50 sorbitol decanoate to sorbitol octanoate. Solution 2 contained a ratio of 75:25 sorbitol decanoate to sorbitol octanoate. Solution 3 contained a ratio of 87.5:12.5 sorbitol decanoate to sorbitol octanoate. The total active ingredients in each solution including controls were 40% and the concentrate solutions were diluted to the ppm concentrations noted in the following table.

TABLE 5

| Level ppm | 1 hr Kill Percentage | | |
|---|---|---|---|
| | Solution 1 | Solution 2 | Solution 3 |
| 40 | 34.12 | 41.57 | 53.56 |
| 200 | 44.04 | 44.07 | 59.36 |
| 400 | 44.78 | 47.45 | 64.91 |
| 1200 | 57.64 | 69.35 | 70.02 |
| 2400 | 60.31 | 68.10 | 72.68 |
| 3200 | 49.03 | 67.41 | 67.80 |
| 4000 | 72.55 | 67.27 | 81.50 |

Unexpectedly it was found that any combination of these two ingredients can be used. Similar results for 1 hr kills were obtained for Pear Psylla.

We claim:

1. A method for treating plants for reducing or eliminating insect pests comprising:
   (a) mixing together sucrose octanoate and sorbitol octanoate, and
   (b) applying mixture to said plants.

2. The method as defined in claim 1 wherein ratio of said sorbitol octanoate to said sucrose octanoate is 50 to 50 in said mixture.

3. The method as defined in claim 1 wherein ratio of said sorbitol octanoate to said sucrose octanoate is 75 to 25 in said mixture.

4. The method as defined in claim 1 wherein ratio of said sorbitol octanoate to said sucrose octanoate is 87.5 to 12.5 in said mixture.

5. The method as defined in claim 1 wherein said mixture is diluted to contain at least 40 ppm up to 4000 ppm of said octanoates.

6. A method for treating plants for reducing or eliminating insect pests comprising:
   (a) mixing together sucrose octanoate and an alcoholic solvent, and
   (b) applying mixture to said plants.

7. The method as defined in claim 6 wherein the alcohol is selected from the group consisting of butanol, propanol, ethanol, and methanol.

8. The method as defined in claim 6 wherein said mixture contains at least 4% alcohol.

9. The method as defined in claim 6 wherein said mixture is diluted to contain at least 40 ppm up to 4000 ppm of said octanoate.

10. A method for treating plants for reducing or eliminating insect pests comprising:
    (a) mixing together sorbitol octanoate and sorbitol decanoate, and
    (b) applying mixture to said plants.

11. The method as defined in claim 10 wherein ratio of said sorbitol decanoate to said sorbitol octanoate is 50 to 50 in said mixture.

12. The method as defined in claim 10 wherein ratio of said sorbitol decanoate to said sorbitol octanoate is 75 to 25 in said mixture.

13. A method as defined in claim 10 wherein ratio of said sorbitol decanoate to said sorbitol octanoate is 87.5 to 12.5 in said mixture.

14. A method as defined in claim 10 wherein said mixture is diluted to contain at least 40 up to 4000 ppm of sorbitol esters.

* * * * *